US009672615B2

United States Patent
Fonte et al.

(10) Patent No.: US 9,672,615 B2
(45) Date of Patent: *Jun. 6, 2017

(54) METHODS AND SYSTEMS FOR ASSESSING IMAGE QUALITY IN MODELING OF PATIENT ANATOMIC OR BLOOD FLOW CHARACTERISTICS

(71) Applicant: HeartFlow, Inc., Redwood City, CA (US)

(72) Inventors: Timothy A. Fonte, San Francisco, CA (US); Leo J. Grady, Millbrae, CA (US); Zhongle Wu, Troy, MI (US); Michiel Schaap, San Mateo, CA (US); Stanley C. Hunley, Menlo Park, CA (US); Souma Sengupta, Cupertino, CA (US)

(73) Assignee: Heartflow, Inc., Redwood City, CA (US)

( * ) Notice: Subject to any disclaimer, the term of this patent is extended or adjusted under 35 U.S.C. 154(b) by 95 days.

This patent is subject to a terminal disclaimer.

(21) Appl. No.: 14/554,653

(22) Filed: Nov. 26, 2014

(65) Prior Publication Data

US 2015/0086093 A1 Mar. 26, 2015

Related U.S. Application Data

(63) Continuation of application No. 14/484,112, filed on Sep. 11, 2014, now Pat. No. 9,008,405, which is a
(Continued)

(51) Int. Cl.
*G06T 7/00* (2017.01)
*A61B 6/00* (2006.01)
(Continued)

(52) U.S. Cl.
CPC ............ *G06T 7/0012* (2013.01); *A61B 5/026* (2013.01); *A61B 5/0261* (2013.01); *A61B 6/032* (2013.01);
(Continued)

(58) Field of Classification Search
CPC ....... A61B 5/026; A61B 5/0261; A61B 6/032; A61B 6/507; A61B 6/5217; A61B 6/5258;
(Continued)

(56) References Cited

U.S. PATENT DOCUMENTS 6,633,686 B1 10/2003 Bakircioglu et al.
6,909,794 B2 6/2005 Caspi
(Continued)

OTHER PUBLICATIONS

Office Action in corresponding European Patent Application No. EP 14713284.9, dated Sep. 16, 2015, (5 pages).
(Continued)

*Primary Examiner* — Siamak Harandi
(74) *Attorney, Agent, or Firm* — Bookoff McAndrews, PLLC

(57) ABSTRACT

Systems and methods are disclosed for assessing the quality of medical images of at least a portion of a patient's anatomy, using a computer system. One method includes receiving one or more images of at least a portion of the patient's anatomy; determining, using a processor of the computer system, one or more image properties of the received images; performing, using a processor of the computer system, anatomic localization or modeling of at least a portion of the patient's anatomy based on the received images; obtaining an identification of one or more image characteristics associated with an anatomic feature of the patient's anatomy based on the anatomic localization or modeling; and calculating, using a processor of the computer system, an image quality score based on the one or
(Continued)

more image properties and the one or more image characteristics.

20 Claims, 10 Drawing Sheets

Related U.S. Application Data continuation of application No. 14/172,554, filed on Feb. 4, 2014, now Pat. No. 8,861,820, which is a continuation of application No. 14/163,589, filed on Jan. 24, 2014, now Pat. No. 8,824,752.

(60) Provisional application No. 61/793,162, filed on Mar. 15, 2013.

(51) Int. Cl.
*A61B 5/026* (2006.01)
*A61B 8/08* (2006.01)
*A61B 6/03* (2006.01)
*G06F 19/00* (2011.01)
*G01R 33/563* (2006.01)

(52) U.S. Cl.
CPC ............ *A61B 6/481* (2013.01); *A61B 6/504* (2013.01); *A61B 6/5217* (2013.01); *A61B 8/0883* (2013.01); *A61B 5/0263* (2013.01); *A61B 6/037* (2013.01); *A61B 6/507* (2013.01); *A61B 6/5258* (2013.01); *A61B 6/5294* (2013.01); *A61B 8/5223* (2013.01); *A61B 2576/02* (2013.01); *G01R 33/5635* (2013.01); *G06F 19/3437* (2013.01); *G06T 2207/10081* (2013.01); *G06T 2207/10088* (2013.01); *G06T 2207/10104* (2013.01); *G06T 2207/10108* (2013.01); *G06T 2207/10132* (2013.01); *G06T 2207/30004* (2013.01); *G06T 2207/30104* (2013.01); *G06T 2207/30168* (2013.01); *G06T 2207/30172* (2013.01); *G06T 2207/30196* (2013.01); *G06T 2210/41* (2013.01)

(58) Field of Classification Search
CPC . A61B 6/5294; A61B 8/5223; G06F 19/3437; G06T 2207/30104; G06T 2207/30168; G06T 2207/30172; G06T 7/0012
See application file for complete search history.

(56) References Cited

U.S. PATENT DOCUMENTS

| | | | |
|---|---|---|---|
| 7,940,970 | B2 | 5/2011 | Levanon et al. |
| 2008/0123927 | A1 | 5/2008 | Miga et al. |
| 2008/0304722 | A1 | 12/2008 | Soenksen |
| 2008/0312893 | A1* | 12/2008 | Denton ............ G01N 35/00613 703/11 |
| 2009/0138318 | A1 | 5/2009 | Hawkins et al. |
| 2010/0069759 | A1 | 3/2010 | Schuhrke et al. |
| 2010/0086189 | A1 | 4/2010 | Wang et al. |
| 2011/0301977 | A1 | 12/2011 | Belcher et al. |
| 2012/0041318 | A1 | 2/2012 | Taylor |
| 2012/0230565 | A1 | 9/2012 | Steinberg et al. |

OTHER PUBLICATIONS

Cemil Kirbas et al., "A Review of Vessel Extraction Techniques and Algorithms", ACM Computing Surveys, vol. 36, No. 2, Jun. 2004, pp. 81-121.
E. Wellnhofer et al.; "Novel non-dimensional approach to comparison of wall shear stress distributions in coronary arteries of different groups of patients", Atherosclerosis, Elsevier Ireland Ltd., IE, vol. 202, No. 2, Feb. 1, 2009, pp. 483-490.
Notification of Transmittal of the International Search Report and the Written Opinion of the International Searching Authority, or the Declaration, date mailed May 30, 2014, issued in International Appln. No. PCT/US2014/019008, filed Feb. 27, 2014.

* cited by examiner

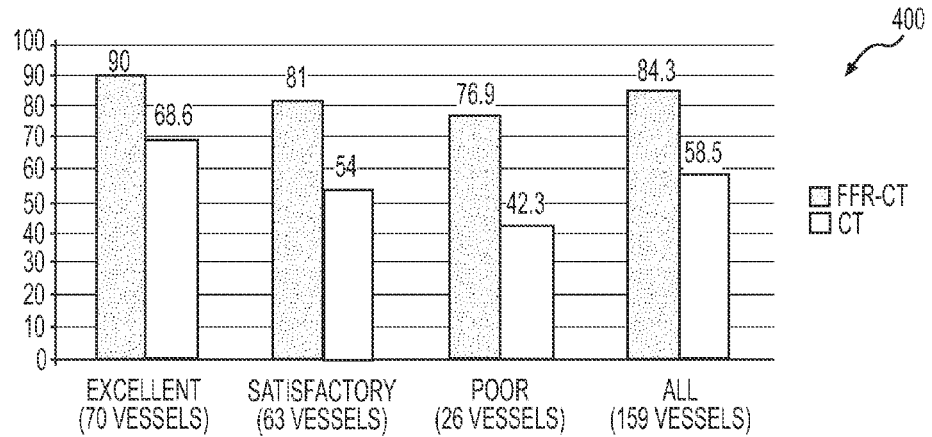

FIG. 8

| ARTIFACT | AMOUNT OF REGION AFFECTED | COMPLETELY OBLITERATES LUMEN OR CAUSES MISSING INFORMATION AND PREVENTS IDENTIFICATION OF DISEASE | CANNOT DETERMINE PRECISE LUMEN BOUNDARY, BUT CAN IDENTIFY DISEASE PRESENT - CAN SEE WHERE MLD WOULD BE | CANNOT DETERMINE PRECISE LUMEN BOUNDARY, BUT CAN IDENTIFY NO DISEASE |
|---|---|---|---|---|
| COMBINATION (NOISE, MOTION, CONTRAST) | FULL SMALL | 10 5 | 10 5 | 5 3 |
| MOTION | FULL SMALL | 10 5 | 10 4 | 4 2 |
| MIS-ALIGNMENT | FULL SMALL | 10 5 | 5 (MISALIGNMENT VS MISSING INFORMATION) 3 | 2 (MISALIGNMENT VS MISSING INFORMATION) 1 |
| NOISE | FULL SMALL | 10 5 | 5 3 | 2 1 |
| BLOOMING | FULL SMALL | N/A N/A | 10 (COMPLETE REGION BLOOMED) 3 | N/A N/A |
| CONTRAST | FULL SMALL | | 1 | |
| OPACIFICATION | FULL SMALL | | 1 | |

FIG. 9

METHODS AND SYSTEMS FOR ASSESSING IMAGE QUALITY IN MODELING OF PATIENT ANATOMIC OR BLOOD FLOW CHARACTERISTICS

PRIORITY

This application is a continuation of U.S. patent application Ser. No. 14/484,112, filed Sep. 11, 2014, which is a continuation of U.S. patent application Ser. No. 14/172,554, filed Feb. 4, 2014 (now U.S. Pat. No. 8,861,820), which is a continuation of U.S. application Ser. No. 14/163,589, filed Jan. 24, 2014, (now U.S. Pat. No. 8,824,752), issued Sep. 2, 2014, which claims the benefit of priority from U.S. Provisional Application No. 61/793,162, filed Mar. 15, 2013, each of which is herein incorporated by reference in its entirety.

TECHNICAL FIELD

Embodiments of the present disclosure relate to methods and systems for assessing medical image quality and, more particularly, to methods and systems for assessing medical image quality in relation to patient-specific modeling of anatomy and/or blood flow.

BACKGROUND

Medical imaging is an important technology used to gain anatomic and physiologic data about a patient's body, organs, tissues, or a portion thereof for clinical diagnosis and treatment planning. Medical imaging includes, but is not limited to, radiography, computed tomography (CT), magnetic resonance imaging (MRI), fluoroscopy, single-photon emission computed tomography (SPECT), positron emission tomography (PET), scintigraphy, ultrasound, and specific techniques such as echocardiography, mammography, intravascular ultrasound, and angiography. Imaging data may be obtained through non-invasive or invasive procedures. The fields of cardiology, neuroscience, oncology, orthopedics, and many others benefit from information obtained in medical imaging.

In the field of cardiology, in particular, it is well known that coronary artery disease may cause the blood vessels providing blood to the heart to develop lesions, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack. A need exists to provide more accurate data relating to coronary lesions, e.g., size, shape, location, functional significance (e.g., whether the lesion impacts blood flow), etc. Patients suffering from chest pain and/or exhibiting symptoms of coronary artery disease may be subjected to one or more tests, such as based on medical imaging, that may provide some indirect evidence relating to coronary lesions.

In addition to CT, SPECT, and PT, the use of medical imaging for noninvasive coronary evaluation may include electrocardiograms, biomarker evaluation from blood tests, treadmill tests, and echocardiography. These noninvasive tests, however, typically do not provide a direct assessment of coronary lesions or assess blood flow rates. The noninvasive tests may provide indirect evidence of coronary lesions by looking for changes in electrical activity of the heart (e.g., using electrocardiography (ECG)), motion of the myocardium (e.g., using stress echocardiography), perfusion of the myocardium (e.g., using PET or SPECT), or metabolic changes (e.g., using biomarkers).

For example, anatomic data may be obtained noninvasively using coronary computed tomographic angiography (CCTA). CCTA may be used for imaging of patients with chest pain and involves using CT technology to image the heart and the coronary arteries following an intravenous infusion of a contrast agent. However, CCTA also cannot provide direct information on the functional significance of coronary lesions, e.g., whether the lesions affect blood flow. In addition, since CCTA is purely a diagnostic test, it can neither be used to predict changes in coronary blood flow, pressure, or myocardial perfusion under other physiologic states (e.g., exercise), nor can it be used to predict outcomes of interventions.

Thus, patients may require an invasive test, such as diagnostic cardiac catheterization, to visualize coronary lesions. Diagnostic cardiac catheterization may include performing conventional coronary angiography (CCA) to gather anatomic data on coronary lesions by providing a doctor with an image of the size and shape of the arteries. CCA, however, does not provide data for assessing the functional significance of coronary lesions. For example, a doctor may not be able to diagnose whether a coronary lesion is harmful without determining whether the lesion is functionally significant. Thus, CCA has led to a procedure referred to as an "oculostenotic reflex," in which interventional cardiologists insert a stent for every lesion found with CCA regardless of whether the lesion is functionally significant. As a result, CCA may lead to unnecessary operations on the patient, which may pose added risks to patients and may result in unnecessary heath care costs for patients.

During diagnostic cardiac catheterization, the functional significance of a coronary lesion may be assessed invasively by measuring the fractional flow reserve (FFR) of an observed lesion. FFR is defined as the ratio of the mean blood pressure downstream of a lesion divided by the mean blood pressure upstream from the lesion, e.g., the aortic pressure, under conditions of increased coronary blood flow, e.g., when induced by intravenous administration of adenosine. Blood pressures may be measured by inserting a pressure wire into the patient. Thus, the decision to treat a lesion based on the determined FFR may be made after the initial cost and risk of diagnostic cardiac catheterization has already been incurred.

To fill the gaps left by each of the pure medical imaging and invasive procedures described above, HeartFlow, Inc. has developed simulation and modeling technology based on patient-specific imaging data. For example, various simulation, modeling, and computational techniques include, but are not limited to: computational mechanics, computational fluid dynamics (CFD), numerical simulation, multi-scale modeling, monte carlo simulation, machine learning, artificial intelligence and various other computational methods to solve mathematical models. These techniques may provide information about biomechanics, fluid mechanics, changes to anatomy and physiology over time, electrophysiology, stresses and strains on tissue, organ function, and neurologic function, among others. This information may be provided at the time of the imaging study or prediction of changes over time as a result of medical procedures or the passage of time and progression of disease.

One illustrative application of computational simulation and modeling is described by HeartFlow, Inc., for modeling vascular blood flow from non-invasive imaging data, including assessing the effect of various medical, interventional, or surgical treatments (see, e.g., U.S. Pat. Nos. 8,386,188; 8,321,150; 8,315,814; 8,315,813; 8,315,812; 8,311,750; 8,311,748; 8,311,747; and 8,157,742). In particular, Heart-Flow, Inc. has developed methods for assessing coronary anatomy, myocardial perfusion, and coronary artery flow, noninvasively, to reduce the above disadvantages of invasive FFR measurements. Specifically, CFD simulations have been successfully used to predict spatial and temporal variations of flow rate and pressure of blood in arteries, including FFR. Such methods and systems benefit cardiologists who diagnose and plan treatments for patients with suspected coronary artery disease, and predict coronary artery flow and myocardial perfusion under conditions that cannot be directly measured, e.g., exercise, and to predict outcomes of medical, interventional, and surgical treatments on coronary artery blood flow and myocardial perfusion.

For the above-described techniques, and many other applications of image-based modeling and simulation, the characteristics and quality of the image data is important. During acquisition of medical imaging data, a variety of artifacts or limitations may exist that affect the quality of the image. For example, settings and capabilities of spatial and temporal resolution, energy-tissue interactions, patient or organ movement, reconstruction algorithms, hardware failures, timing or acquisition, detector sensitivity, medication or contrast media administered, patient preparation, and various other factors can affect the resulting image quality. Effects include, but are not limited to, poor resolution, motion or blurring artifacts, high noise, low contrast of tissue, poor perfusion, partial volume effect, distortion, clipping of structures, shadowing, etc. Since these quality issues may affect the performance and accuracy of models and simulations based on the imaging data, there is a need to determine if image quality is suitable or to determine the effect of image quality on modeling and simulation results.

As a result, there is a need for methods and systems for assessing and quantifying medical image quality and, more particularly, to methods and systems for assessing and quantifying medical image quality in relation to patient-specific modeling of blood flow. The foregoing general description and the following detailed description are exemplary and explanatory only and are not restrictive of the disclosure.

SUMMARY

In accordance with an embodiment, methods are disclosed for assessing the quality of medical images of at least a portion of a patient's anatomy, using a computer system. One method includes receiving one or more images of at least a portion of the patient's anatomy; determining, using a processor of the computer system, one or more image properties of the received images; performing, using a processor of the computer system, anatomic localization or modeling of at least a portion of the patient's anatomy based on the received images; obtaining an identification of one or more image characteristics associated with an anatomic feature of the patient's anatomy based on the anatomic localization or modeling; and calculating, using a processor of the computer system, an image quality score based on the one or more image properties and the one or more image characteristics.

In accordance with another embodiment, systems are disclosed for assessing the quality of medical images of at least a portion of a patient's anatomy. One system includes a digital storage device storing instructions for assessing the quality of medical images of at least a portion of a patient's anatomy; and a processor configured to execute the instructions to perform a method including: receiving one or more images of at least a portion of the patient's anatomy; determining, using a processor of the computer system, one or more image properties of the received images; performing, using a processor of the computer system, anatomic localization or modeling of at least a portion of the patient's anatomy based on the received images; obtaining an identification of one or more image characteristics associated with an anatomic feature of the patient's anatomy based on the anatomic localization or modeling; and calculating, using a processor of the computer system, an image quality score based on the one or more image properties and the one or more image characteristics.

In accordance with another embodiment, a non-transitory computer readable medium is disclosed for use on at least one computer system containing computer-executable programming instructions for assessing the quality of medical images of at least a portion of a patient's anatomy, that when executed by the at least one computer system, cause the performance of a method comprising: receiving one or more images of at least a portion of the patient's anatomy; determining, using a processor of the computer system, one or more image properties of the received images; performing, using a processor of the computer system, anatomic localization or modeling of at least a portion of the patient's anatomy based on the received images; obtaining an identification of one or more image characteristics associated with an anatomic feature of the patient's vasculature based on the anatomic localization or modeling; and calculating, using a processor of the computer system, an image quality score based on the one or more image properties and the one or more image characteristics.

Additional embodiments and advantages will be set forth in part in the description which follows, and in part will be obvious from the description, or may be learned by practice of the disclosure. The embodiments and advantages will be realized and attained by means of the elements and combinations particularly pointed out below.

BRIEF DESCRIPTION OF THE DRAWINGS

The accompanying drawings, which are incorporated in and constitute a part of this specification, illustrate several embodiments and together with the description, serve to explain the principles of the disclosure.

FIG. 8 is an exemplary bar graph depicting comparisons between performance or accuracy of fractional flow reserve and computed tomography, based on image quality, by number of vessels, according to various exemplary embodiments;

FIG. 9 is a table depicting an exemplary rubric for scoring image characteristics based on lumen features of cardiovascular vessels, according to various exemplary embodiments.

DESCRIPTION OF THE EMBODIMENTS

Figure 1:
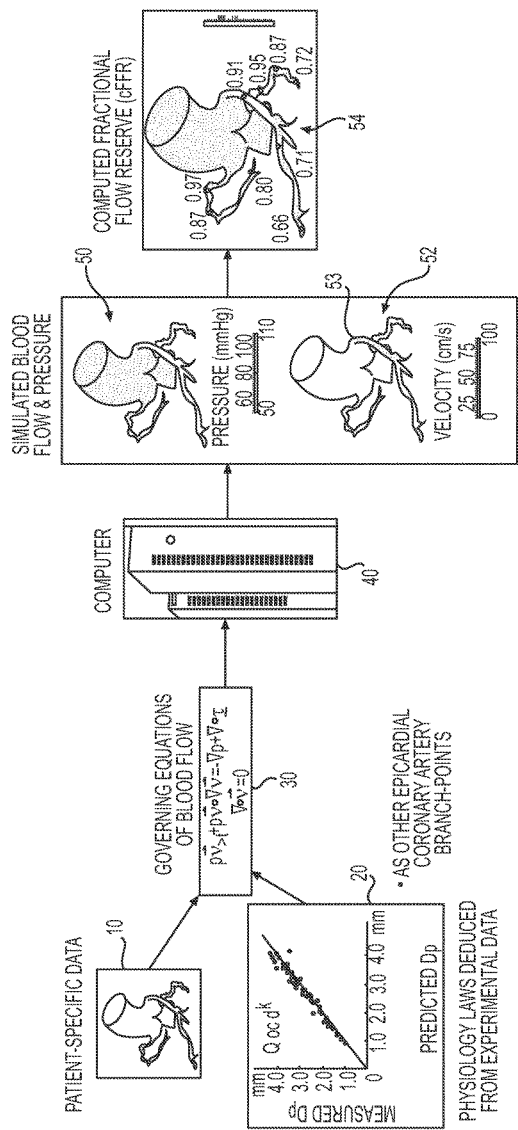
FIG. 1 is a schematic diagram of a system for determining various information relating to coronary blood flow in a specific patient, according to an exemplary embodiment.

Reference will now be made in detail to exemplary embodiments, examples of which are illustrated in the accompanying drawings. Wherever possible, the same reference numbers will be used throughout the drawings to refer to the same or like parts.

Overview

The present disclosure relates to assessing and quantifying the quality of medical images. In one embodiment, the present disclosure describes systems and methods for assessing image quality for the purpose of predicting or analyzing the accuracy and performance of medical imagery simulation and modeling. In one embodiment, a method of assessing medical image quality includes: receiving image data and possibly patient information; performing assessment of image quality by computer automated, user-guided, or a combination of means at a local and/or global level; and generating image quality metrics that are regional (e.g., for a vessel) or for an entire dataset or multiple datasets. In one embodiment, a method of assessing medical image quality may include applying image quality metrics for one or more of: (i) evaluating whether imaging data is suitable to achieve desired simulation accuracy, precision, and/or performance; (ii) estimating the accuracy, precision, or confidence of simulation results; (iii) guiding simulation or modeling techniques best suited to achieve desired accuracy, precision, and/or performance; and/or (iv) selecting, combining, or correcting the best data from a variety of received data in order to achieve desired accuracy, precision, and/or performance.

In one embodiment, quality issues or anomalies may include, but are not limited to, low contrast, noise, motion or blurring, misregistration or misalignment, low resolution, partial volume effect, beam hardening, clipped anatomy excluded from the scan, streaking, scanner failures, missing data, and/or inconsistent contrast timing. If these issues affect information of interest, such as the anatomy of coronary arteries, in such a manner that they may affect the quality, accuracy, or performance of blood flow models and simulations, then it may be desirable to detect and score the image quality issues. Then, the quality of the imaging data may be analyzed for its effect on the ability to extract the desired information from patient images.

In an exemplary embodiment, the disclosed methods and systems involve the use of at least one computer configured to receive patient-specific imaging data containing at least some of the coronary vasculature. In order to model coronary blood flow from imaging data, at least some portions of the coronary artery anatomy may be measured, modeled, segmented, or estimated. Additionally, at least some portions of the heart, aorta, myocardium, ventricles, valves, veins and other structures of the heart may be measured, modeled, segmented, or estimated. Along with anatomic representations, information regarding contrast levels, contrast gradients, or other image-analysis metrics may be extracted to inform the model.

Thus, in such an exemplary embodiment, methods and systems are disclosed for determining image quality from patient-specific imaging data for the purposes of blood flow modeling and simulation. Such an embodiment may include the assessment of coronary computed topographic angiography (cCTA) imaging data to simulate information including, but not limited to, coronary blood flow, velocity, pressure, plaque and wall stress, and fractional flow reserve (FFR). The methods and systems may be adopted to other areas of the vasculature including, but not limited to, carotid, peripheral, abdominal, renal, and cerebral, as well as to other imaging modalities including, but not limited to, MRI, PET, SPECT, ultrasound, and angiography.

Accordingly, in certain embodiments that follow, systems and methods for assessing and quantifying image quality are described, for purposes of example, in the context of images of coronary vasculature. More specifically, in certain embodiments, systems and methods for assessing and quantifying image quality are described, for purposes of example, in the context of analyzing the quality of images used in modeling patient-specific coronary vasculature, and simulating blood flow through patient-specific coronary vasculature. However, it should be appreciated that the presently disclosed techniques for assessing and quantifying image quality are equally applicable to evaluating and manipulating medical imagery in relation to any anatomy, or in relation to any cardiovascular evaluation, among any other medical diagnostic techniques.

Exemplary Cardiovascular Context

In one embodiment, the present disclosure relates to methods and systems for assessing image quality in the context of determining blood flow information in a specific patient, using information retrieved from the patient noninvasively. Various embodiments of such a method and system are described in greater detail in U.S. Pat. No. 8,315,812, filed Jan. 25, 2011, and entitled "Method and System for Patient-Specific Modeling of Blood Flow," which is hereby incorporated by reference in its entirety.

In some embodiments, the information determined by the method and system may relate to blood flow in the patient's coronary vasculature. Alternatively, the determined information may relate to blood flow in other areas of the patient's vasculature, such as carotid, peripheral, abdominal, renal, and cerebral vasculature. The coronary vasculature includes a complex network of vessels ranging from large arteries to arterioles, capillaries, venules, veins, etc. The coronary vasculature circulates blood to and within the heart and includes an aorta that supplies blood to a plurality of main coronary arteries (e.g., the left anterior descending (LAD) artery, the left circumflex (LCX) artery, the right coronary (RCA) artery, etc.), which may further divide into branches of arteries or other types of vessels downstream from the aorta and the main coronary arteries. Thus, the exemplary method and system may determine information relating to blood flow within the aorta, the main coronary arteries, and/or other coronary arteries or vessels downstream from the main coronary arteries. Although the aorta and coronary arteries (and the branches that extend therefrom) are discussed below, the disclosed method and system may also apply to other types of vessels.

In an exemplary embodiment, the information determined by the disclosed methods and systems may include, but is not limited to, various blood flow characteristics or parameters, such as blood flow velocity, pressure (or a ratio thereof), flow rate, and FFR at various locations in the aorta, the main coronary arteries, and/or other coronary arteries or vessels downstream from the main coronary arteries. This information may be used to determine whether a lesion is functionally significant and/or whether to treat the lesion. This information may be determined using information obtained noninvasively from the patient. As a result, the decision whether to treat a lesion may be made without the cost and risk associated with invasive procedures.

FIG. 1 shows aspects of a system for providing information relating to coronary blood flow in a specific patient, according to an exemplary embodiment. A three-dimensional model 10 of the patient's anatomy may be created using data obtained noninvasively from the patient as will be described below in more detail. Other patient-specific information may also be obtained noninvasively. In an exemplary embodiment, the portion of the patient's anatomy that is represented by the three-dimensional model 10 may include at least a portion of the aorta and a proximal portion of the main coronary arteries (and the branches extending or emanating therefrom) connected to the aorta.

Various physiological laws or relationships 20 relating to coronary blood flow may be deduced, e.g., from experimental data as will be described below in more detail. Using the three-dimensional anatomical model 10 and the deduced physiological laws 20, a plurality of equations 30 relating to coronary blood flow may be determined as will be described below in more detail. For example, the equations 30 may be determined and solved using any numerical method, e.g., finite difference, finite volume, spectral, lattice Boltzmann, particle-based, level set, finite element methods, etc. The equations 30 can be solved to determine information (e.g., pressure, velocity, FFR, etc.) about the coronary blood flow in the patient's anatomy at various points in the anatomy represented by the model 10.

The equations 30 may be solved using a computer system 40. Based on the solved equations, the computer system 40 may output one or more images or simulations indicating information relating to the blood flow in the patient's anatomy represented by the model 10. For example, the image(s) may include a simulated blood pressure model 50, a simulated blood flow or velocity model 52, a computed FFR (cFFR) model 54, etc., as will be described in further detail below. The simulated blood pressure model 50, the simulated blood flow model 52, and the cFFR model 54 provide information regarding the respective pressure, velocity, and cFFR at various locations along three dimensions in the patient's anatomy represented by the model 10. cFFR may be calculated as the ratio of the blood pressure at a particular location in the model 10 divided by the blood pressure in the aorta, e.g., at the inflow boundary of the model 10, under conditions of increased coronary blood flow, e.g., conventionally induced by intravenous administration of adenosine.

In an exemplary embodiment, the computer system 40 may include one or more non-transitory computer-readable storage devices that store instructions that, when executed by a processor, computer system, etc., may perform any of the actions described herein for providing various sources of information relating to blood flow in the patient. The computer system 40 may include a desktop or portable computer, a workstation, a server, a personal digital assistant, or any other computer system. The computer system 40 may include a processor, a read-only memory (ROM), a random access memory (RAM), an input/output (I/O) adapter for connecting peripheral devices (e.g., an input device, output device, storage device, etc.), a user interface adapter for connecting input devices such as a keyboard, a mouse, a touch screen, a voice input, and/or other devices, a communications adapter for connecting the computer system 40 to a network, a display adapter for connecting the computer system 40 to a display, etc. For example, the display may be used to display the three-dimensional model 10 and/or any images generated by solving the equations 30, such as the simulated blood pressure model 50, the simulated blood flow model 52, and/or the cFFR model 54.

Figure 2:
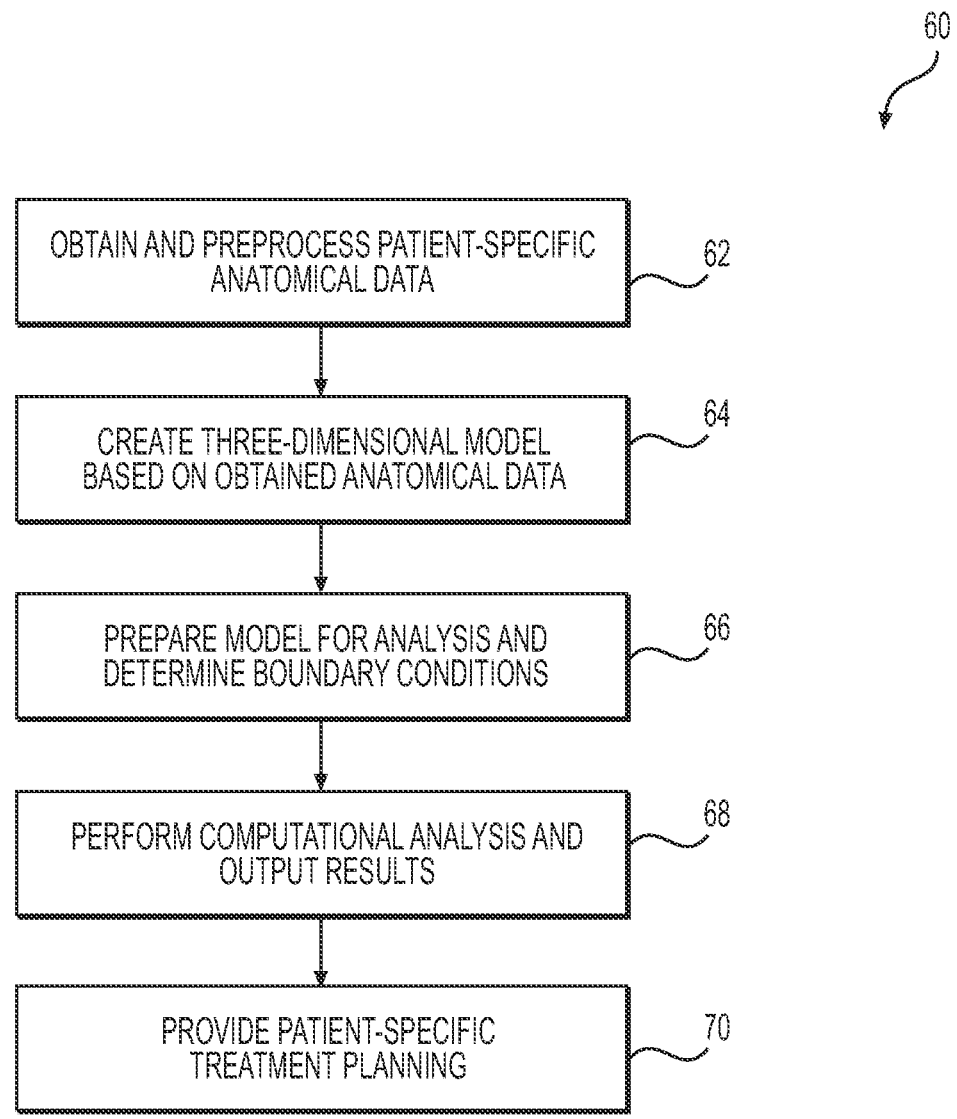
FIG. 2 is a flow chart of a method for determining various information relating to coronary blood flow in a specific patient, according to an exemplary embodiment.

FIG. 2 shows aspects of a method 60 for providing various sources of information relating to blood flow in a specific patient, according to another exemplary embodiment. The method may include obtaining patient-specific anatomical data, such as information regarding the patient's anatomy (e.g., at least a portion of the aorta and a proximal portion of the main coronary arteries (and the branches extending therefrom) connected to the aorta), and preprocessing the data (step 62). The patient-specific anatomical data may be obtained noninvasively, e.g., by CCTA.

A three-dimensional model of the patient's anatomy may be created based on the obtained anatomical data (step 64). For example, the three-dimensional model may be the three-dimensional model 10 of the patient's anatomy described above in connection with FIG. 1.

The three-dimensional model may be prepared for analysis and boundary conditions may be determined (step 66). For example, the three-dimensional model 10 of the patient's anatomy described above in connection with FIG. 1 may be trimmed and discretized into a volumetric mesh, e.g., a finite element or finite volume mesh. The volumetric mesh may be used to generate the equations 30 described above in connection with FIG. 1.

Boundary conditions may also be assigned and incorporated into the equations 30 described above in connection with FIG. 1. The boundary conditions provide information about the three-dimensional model 10 at its boundaries, e.g., inflow boundaries, outflow boundaries, vessel wall boundaries, etc. The inflow boundaries may include the boundaries through which flow is directed into the anatomy of the three-dimensional model, such as at an end of the aorta near the aortic root. Each inflow boundary may be assigned, e.g., with a prescribed value or field for velocity, flow rate, pressure, or other characteristic, by coupling a heart model and/or a lumped parameter model to the boundary, etc. The outflow boundaries may include the boundaries through which flow is directed outward from the anatomy of the three-dimensional model, such as at an end of the aorta near the aortic arch, and the downstream ends of the main coronary arteries and the branches that extend therefrom. Each outflow boundary can be assigned, e.g., by coupling a lumped parameter or distributed (e.g., a one-dimensional wave propagation) model. The prescribed values for the inflow and/or outflow boundary conditions may be determined by noninvasively measuring physiologic characteristics of the patient, such as, but not limited to, cardiac output (the volume of blood flow from the heart), blood pressure, myocardial mass, etc. The vessel wall boundaries may include the physical boundaries of the aorta, the main coronary arteries, and/or other coronary arteries or vessels of the three-dimensional model 10.

The computational analysis may be performed using the prepared three-dimensional model and the determined boundary conditions (step 68) to determine blood flow information for the patient. For example, the computational analysis may be performed with the equations 30 and using the computer system 40 described above in connection with FIG. 1 to produce the images described above in connection with FIG. 1, such as the simulated blood pressure model 50, the simulated blood flow model 52, and/or the cFFR model 54.

The method may also include providing patient-specific treatment options using the results (step 70). For example, the three-dimensional model 10 created in step 64 and/or the boundary conditions assigned in step 66 may be adjusted to model one or more treatments, e.g., placing a coronary stent in one of the coronary arteries represented in the three-dimensional model 10 or other treatment options. Then, the computational analysis may be performed as described above in step 68 in order to produce new images, such as updated versions of the blood pressure model 50, the blood flow model 52, and/or the cFFR model 54. These new images may be used to determine a change in blood flow velocity and pressure if the treatment option(s) are adopted.

The systems and methods disclosed herein may be incorporated into a software tool accessed by physicians to provide a noninvasive means to quantify blood flow in the coronary arteries and to assess the functional significance of coronary artery disease. In addition, physicians may use the software tool to predict the effect of medical, interventional, and/or surgical treatments on coronary artery blood flow. The software tool may prevent, diagnose, manage, and/or treat disease in other portions of the cardiovascular system including arteries of the neck (e.g., carotid arteries), arteries in the head (e.g., cerebral arteries), arteries in the thorax, arteries in the abdomen (e.g., the abdominal aorta and its branches), arteries in the arms, or arteries in the legs (e.g., the femoral and popliteal arteries). The software tool may be interactive to enable physicians to develop optimal personalized therapies for patients.

For example, the software tool may be incorporated at least partially into a computer system, e.g., the computer system 40 shown in FIG. 1 used by a physician or other user. The computer system may receive data obtained noninvasively from the patient (e.g., data used to create the three-dimensional model 10, data used to apply boundary conditions or perform the computational analysis, etc.). For example, the data may be input by the physician or may be received from another source capable of accessing and providing such data, such as a radiology or other medical lab. The data may be transmitted via a network or other system for communicating the data, or directly into the computer system. The software tool may use the data to produce and display the three-dimensional model 10 or other models/meshes and/or any simulations or other results determined by solving the equations 30 described above in connection with FIG. 1, such as the simulated blood pressure model 50, the simulated blood flow model 52, and/or the cFFR model 54. Thus, the software tool may perform steps 62-70. In step 70, the physician may provide further inputs to the computer system to select possible treatment options, and the computer system may display to the physician new simulations based on the selected possible treatment options. Further, each of steps 62-70 shown in FIG. 2 may be performed using separate software packages or modules.

Alternatively, the software tool may be provided as part of a web-based service or other service, e.g., a service provided by an entity that is separate from the physician. The service provider may, for example, operate the web-based service and may provide a web portal or other web-based application (e.g., run on a server or other computer system operated by the service provider) that is accessible to physicians or other users via a network or other methods of communicating data between computer systems. For example, the data obtained noninvasively from the patient may be provided to the service provider, and the service provider may use the data to produce the three-dimensional model 10 or other models/meshes and/or any simulations or other results determined by solving the equations 30 described above in connection with FIG. 1, such as the simulated blood pressure model 50, the simulated blood flow model 52, and/or the cFFR model 54. Then, the web-based service may transmit information relating to the three-dimensional model 10 or other models/meshes and/or the simulations so that the three-dimensional model 10 and/or the simulations may be displayed to the physician on the physician's computer system. Thus, the web-based service may perform steps 62-70 and any other steps described below for providing patient-specific information. In step 70, the physician may provide further inputs, e.g., to select possible treatment options or make other adjustments to the computational analysis, and the inputs may be transmitted to the computer system operated by the service provider (e.g., via the web portal). The web-based service may produce new simulations or other results based on the selected possible treatment options, and may communicate information relating to the new simulations back to the physician so that the new simulations may be displayed to the physician.

Image Quality Assessment

The above-described techniques for computational modeling for noninvasively calculating FFR may benefit from assessments of image quality. Accordingly, the present disclosure describes methods and systems for quantifying and assessing the effects of image quality of the available data on the anatomic and mathematical models used in simulating blood flow characteristics. In addition, the present disclosure describes methods and systems for assessing the uncertainty of vessel and other anatomic models based on local and global image properties; and computing confidence intervals of simulated blood flow calculations based on predicted uncertainty.

In an exemplary embodiment, methods and systems may implement at least one computer configured to detect and score image quality issues. In an exemplary embodiment, coronary imaging data is analyzed by a combination of automated and user-guided methods using at least one computer system. As will be described in more detail below, the disclosed methods and systems may be fully automated, fully user-guided, or both automated and user-guided. The disclosed methods and systems may be configured to perform an assessment that may include an evaluation or quantification of one or more of the potential image quality issues listed below:

image resolution
    slice thickness
    reconstruction kernel
    number of scanner slices
    missing slices or missing data
    phase of acquisition medication provided at time of acquisition
heart rate at time of acquisition
anatomic data that is desired but not included in the image data
presence of anatomic abnormalities
presence of implanted devices or prior surgeries
contrast level
noise level
contrast to noise ratio
misregistration or misalignment
motion or blurring
partial volume effect or blooming
beam hardening
general uninterpretable or poorly defined regions In an exemplary embodiment, these issues may be detected at a global level, local level, or both global and local levels. A global level issue may involve detecting an image quality issue based on the entire image volume, and may in some cases be referred to as an "image property." A local level issue may involve the detection space of a particular region, e.g., around some or all of the coronary arteries, coronary plaque, along one or more vessel centerlines, etc., and may in some cases be referred to as an "image characteristic."

In an exemplary embodiment, systems and methods for determining and assessing image quality may use a combination of automated and user-guided quantitative and qualitative assessment of the local and global image quality issues, based on the previously mentioned quality issues.

Image quality issues, such as CT imaging artifacts may come from a plurality of sources including: (i) physical-based sources, such as from tube (kVP, mA) and photons (fluctuation, starvation), beam hardening (streaks, dark bands, etc.), partial volume (blooming), undersampling (blooming), and gantry rotation speed; (ii) patient-based sources, such as heart rate, regular rhythm (motion), metal material, and BMI (beam hardening); (iii) scanner-based sources, such as detector array entities out of calibration, or reconstruction kernels and methods; and/or (iv) protocol-based sources, such as Beta blockers administration (to lower HR), contrast agent administration (high concentration, flow rate, single, dual, triple phase), contrast timing control, etc., ECG sync and correction, nitroglycerin (to enlarge vessel and increase opacification), and left vs. left+ right heart opacification.

Figure 3:
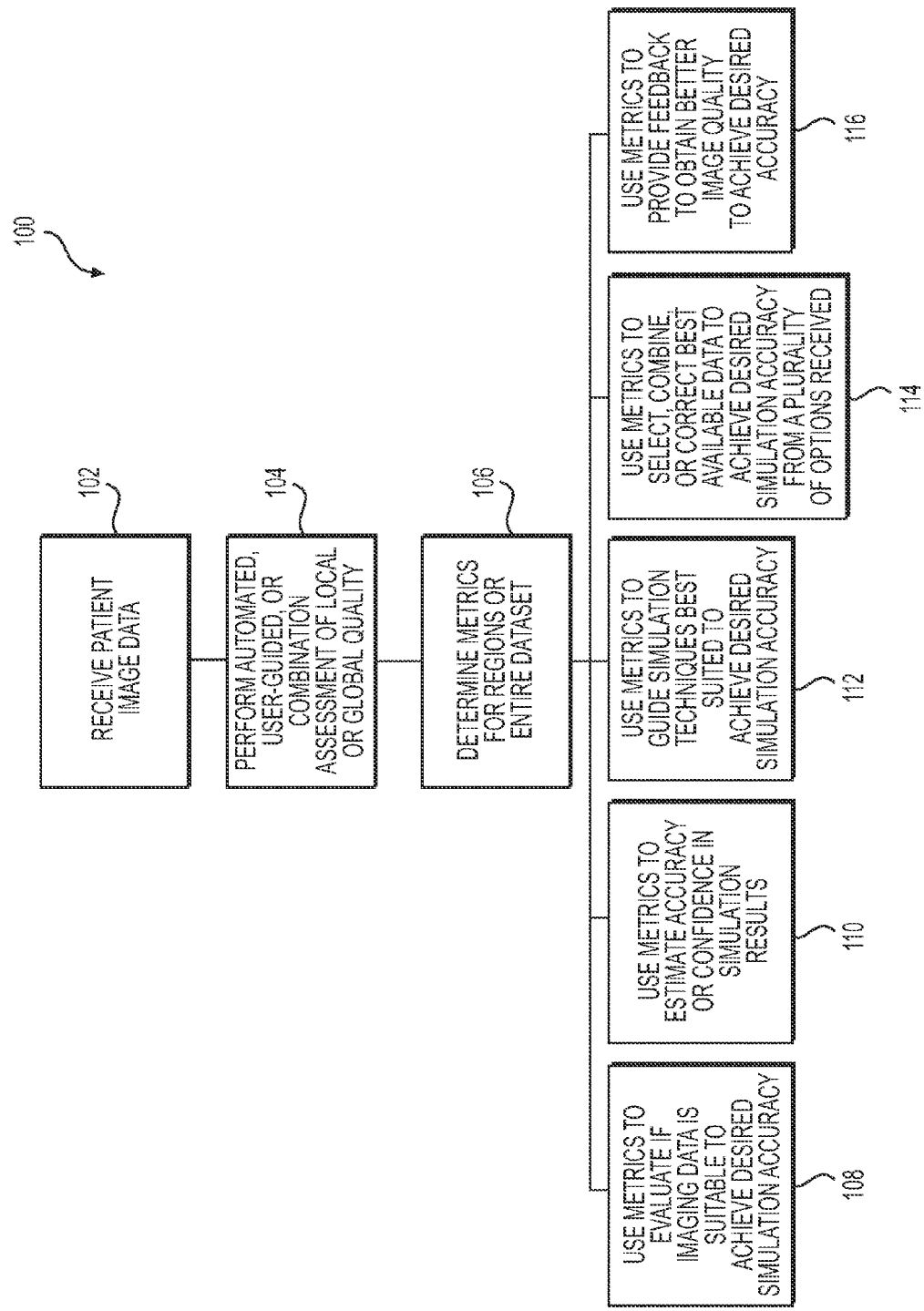
FIG. 3 is a flow chart that describes an exemplary method for assessing medical image quality, generating image quality metrics, and using image quality metrics, according to various exemplary embodiments.

FIG. 3 is a flow chart that describes an exemplary method 100 for assessing medical image quality, generating image quality metrics, and using image quality metrics, according to various exemplary embodiments. In one embodiment, method 100 includes receiving patient image data (step 102). Specifically, in accordance with one embodiment, step 102 may include implementing at least one computer system for determining image quality for simulation and modeling by receiving patient-specific data regarding the patient's body, organs, tissue, or portion thereof. For example, step 102 may include obtaining patient-specific data 10 at computer system 40, or any other computational system (which may be, but is not limited to: a computer, laptop, mobile phone, mobile tablet, DSP, cloud computing system, server farm, etc.).

Method 100 may include performing automated, user-guided, or combined automated and user-guided assessment of local and/or global quality of the received image data (step 104). For example, in an automated embodiment, a computer system may automatically determine both global quality assessments of an entire image or group of images, and local quality assessments of specific portions of a single image or portions of a patient's imaged anatomy. In a user-guided embodiment, a computer system may prompt a user to determine and enter global quality assessments of an entire image or group of images, and determine local quality assessments of specific portions of a single image or portions of a patient's imaged anatomy. In certain embodiments, certain aspects of the local and/or global quality assessments may be formed by any combination of automated and user-guided assessment.

The at least one computer system and method may assess or score a single, various, or combinations of features of image quality to generate image quality metrics for regions of interest or for an entire image dataset (step 106). Specifically, the at least one computer system may use the scores to formulate a regional or dataset image quality metric based on the evaluated features of image quality. The at least one computer system may use the results of the image quality assessment as an input to perform modeling or simulation with the patient-specific data. However, in addition to modeling and simulation of patient-specific data, such as blood flow, the image quality metrics may be used as inputs for any other activities or assessments.

In one embodiment, method 100 may include using the generated metrics to evaluate if imaging data is suitable to achieve a desired simulation accuracy (step 108). For example, method 100 may include using the results of the image quality assessment to accept or reject the image data for modeling or simulation based on predetermined criteria related to accuracy, precision, performance, or other requirements. In addition, method 100 may include using the results of the image quality assessment to estimate performance metrics (e.g., time to complete analysis, cost of analysis) or make a decision based on those metrics to perform or not perform modeling or simulation with the patient-specific data using at least one computer system. For example, a computer system may compute and display a time to complete analysis, based on the results of the image quality assessment. In addition, or alternatively, the computer system may compute and display a cost of analysis, based on the results of the image quality assessment. In addition, or alternatively, the computer system may display and/or transmit a recommendation or requirement to perform or not perform modeling or simulation with the patient-specific data using at least one computer system, based on the results of the image quality assessment. Any of such computed information, such as computed time to complete analysis, cost of analysis, and/or perform/not perform analysis may be displayed to a physician, technician, or any other healthcare provider, whether through an electronic display and/or over an electronic network.

In accordance with another embodiment, method 100 may include using the generated metrics to estimate accuracy or confidence in simulation results (step 110). For example, method 100 may include using the results of the image quality assessment to perform modeling or simulation, and output results with a confidence metric (e.g., errors, percent confidence, confidence intervals, accuracy or precision estimates) associated with the simulation results.

In accordance with another embodiment, method 100 may include using the generated metrics to guide simulation techniques best suited to achieve desired simulation accuracy (step 112). For example, method 100 may include using the results of the image quality assessment to model or simulate using different techniques or algorithms in the entire image data set or relevant affected portions depending on the image quality assessment to enhance or achieve desired performance, accuracy, precision, or other requirements.

In accordance with another embodiment, method 100 may include using the generated metrics to select, combine, or correct best available data to achieve desired simulation accuracy from a plurality of options received (step 114). For example, method 100 may include using the results of the image quality assessment to correct for image quality issues prior to performing modeling or simulation, to enhance or achieve desired performance, accuracy, precision, or other requirements. In addition or alternatively, method 100 may include using the results of the image quality assessment to select the dataset from a multitude of available data (e.g., alternate series or reconstructions) that is most appropriate for performing modeling or simulation, to enhance or achieve desired performance, accuracy, precision, or other requirements. In addition or alternatively, method 100 may include using the results of the image quality assessment to combine various pieces of different imaging data (e.g., other phases or other reconstructions or modalities) to compensate for image quality issues and perform modeling or simulation with the patient-specific data using at least one computer system, to enhance or achieve desired performance, accuracy, precision, or other requirements.

In accordance with another embodiment, method 100 may include using the generated metrics to provide feedback to obtain better image quality to achieve desired accuracy (step 116). For example, method 100 may include using the results of the image quality assessment to assess or score a single, various, or combination of features of image quality in a timeframe that allows feedback to be provided to the personnel providing the imaging data such that they could correct, redo, or update the imaging data to meet some predefined criteria to enhance or achieve desired performance, accuracy, precision, or other requirements. Using the updated or corrected image data, the at least one computer system and method may perform one or more additional iterations of modeling or simulation.

Figure 4:
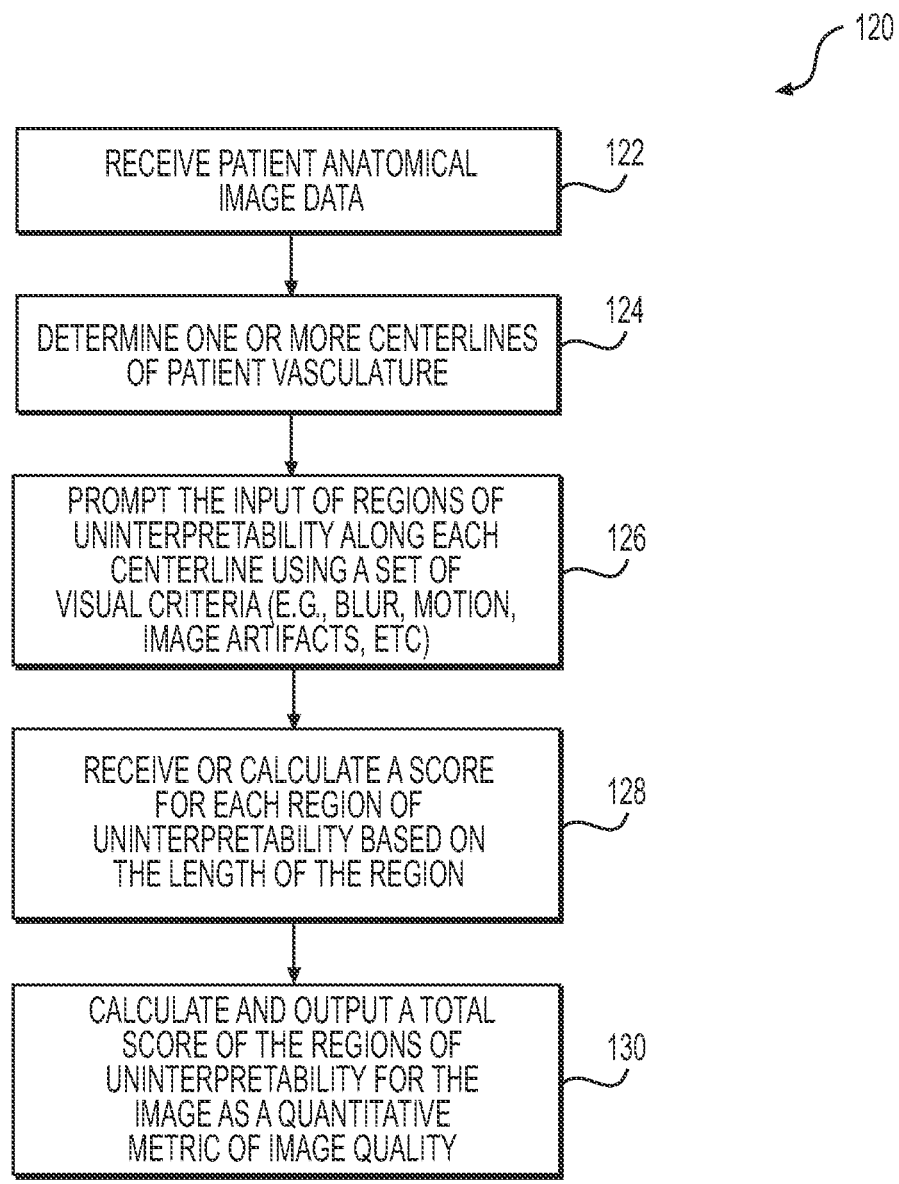
FIG. 4 is a flow chart that describes an exemplary method for enabling and performing user-guided assessment of medical image quality, according to an exemplary embodiment.

FIG. 4 is a flow chart that describes an exemplary method 120 for performing user-guided assessment of image quality, according to an exemplary embodiment. As shown in FIG. 4, in one embodiment, method 120 may include receiving patient anatomical image data (step 122). For example, step 122 may include obtaining image data 10 at a computer system 40, consistent with any of the disclosure of FIGS. 1 and 2 above. Method 120 may further include determining one or more centerlines of patient vasculature (step 124). For example, step 124 may include using a processor of computer system 40 to automatically identify one or more centerlines of patient vasculature, consistent with any of the disclosure of FIGS. 1 and 2 above. In one embodiment, the processor of computer system 40 may add centerlines to the primary vessels (RCA, LAD, and LCX), or any other vessels greater than 2 mm in diameter.

Method 120 may further include prompting a user to input image quality issues, image anomalies, image artifacts, or other "regions of uninterpretability" along each centerline using a set of visual criteria (e.g., blur, motion, image artifacts, etc.) (step 126). For example, a processor of computer system 40 may initiate the display of one or more images and centerlines, and prompt a user to review and inspect the images, and to enter inputs of image quality issues upon finding any misregistration artifacts, blurring, stents, undesirable contrast-to-noise ratio, motion artifacts, blooming artifacts, calcium, scanner errors, missing slices, incomplete data, and so on. For example, the processor of computer system 40 may generate user interface elements that a user can manipulate to indicate that the user identifies any of the image quality issues described herein, along with certain characteristics of location, quantity, or extent of those issues. In one embodiment, either the user or the processor of computer system 40 may characterize each region of uninterpretability as being either short (e.g., 0-5 mm) or long (e.g., greater than 5 mm).

In one embodiment, users may be prompted to identify contrast timing and noise as "good" if an image exhibits high contrast, low noise, and mild right contrast; as "marginal" if an image exhibits moderate contrast, noise, and high right contrast; and as "poor" if an image exhibits low contrast, high noise, and high right contrast. In one embodiment, users may be prompted to identify misregistration as "good" if an image exhibits no misregistration affecting lumen geometry; as "marginal" if an image exhibits misregistration artifacts that are nearly perpendicular to the vessel and can be corrected; and as "poor" if an image exhibits misregistration that cannot be corrected or that exists in an area of disease such that the lumen cannot be determined. In one embodiment, users may be prompted to identify motion as "good" if the motion does not affect the lumen or plaque; as "marginal" if the image reflects that the lumen is affected, but the vessel can be interpreted and modeled with assumptions; and as "poor" if the image reflects that the lumen interpretability is severely affected by motion. In one embodiment, users may be prompted to identify blooming as "good" if mild blooming does not affect lumen interpretability; as "marginal" if a high degree of blooming may require correction but the image still retains lumen visibility; and as "poor" if severe blooming artifact completely obscures the lumen.

Method 120 may further include receiving or calculating a score for each region of uninterpretability based on the length of the region (step 128). In an exemplary embodiment, scores for image quality issues—whether on a qualitative scale (e.g., Likert scale) or quantitative measures—may be determined and analyzed for how they impact or predict modeling and simulation accuracy, precision, and performance. The image quality assessment may have absolute failure criteria in which a dataset is deemed unacceptable, it may have various metrics that are scored, combined, and weighted over a region, vessel, or entire dataset, or it may have a combination of both. For example, in certain embodiments, an automatic fail may be triggered whenever some single or combined image quality issue(s) results in 25% or more of an artery being indiscernible (whether due to noise, motion, blooming, poor contrast, misregistration, etc.).

In an exemplary embodiment, metrics may be generated for either a region (e.g., vessel) or dataset by the image quality scoring system and method based on ratings of at least some of the image quality issues described previously. In one embodiment, each region of uninterpretability may receive a score based on length (e.g., in one embodiment: 1.5 for short, and 3 for long). In one embodiment, a score to reject a patient's images (i.e., a "case") may involve a score of 6 for a single main vessel, a score of 8 for an entire case, and/or a so-called "red flag" that has been assigned a score of 10.

FIG. 9 depicts a table of an exemplary rubric for scoring image characteristics based on lumen features of cardiovascular vessels, according to various exemplary embodiments. Specifically, FIG. 9 depicts one exemplary embodiment of a scoring rubric for assigning scores to regions of uninterpretability or other image quality issues. For example, as shown in the exemplary rubric of FIG. 9, a different score may be assigned to each characteristic (i.e., either combination (noise, motion, contrast), motion, mis-alignment, noise, blooming, contrast, or opacification) based on an amount of region affected (e.g., "full" or "small," or "long" or "short"), and based on whether the identified characteristic: (i) completely obliterates the lumen or causes missing information and prevents identification of disease; (ii) prevents determination of precise lumen boundary, but enables identification of disease present (e.g., shows where minimal luminal diameter ("MLD") would be); or (iii) prevents determination of precise lumen boundary and prevents identification of disease. It should be appreciated that the scoring rubric of FIG. 9 is only an example, and that any alternative scoring mechanisms are contemplated within the scope of this disclosure. For example, the scoring system may be inverted such that lower scores indicate lower image quality, whereas higher scores indicate higher image quality. Alternatively or additionally, the scoring system may be based on an exponential, logarithmic, or fractional scale. Alternatively or additionally, the scoring system may be generated based on a color-coded and/or letter-grade scale, where a color and/or letter indicates some quality level of the scored images.

In certain embodiments, the image quality scores may be weighted and combined with other factors including but not limited to: magnitude of effect, size of the issue, regions affected, issue type (e.g., noise or motion), presence/absence of disease, vessel size, location in the heart, uncertainty in lumen definition, combination with other issues, visual interpretability, algorithm confidence, etc. A function for regions or datasets may be derived that use some, all, or additional weighting factors. One such example is presented below:

$$Quality_{region} = f(\Sigma_i^{vessel} issue_i * magnitude * type * disease * size * vesselsize * location * lumenuncertainty)$$

$$Quality_{dataset} = f(\Sigma_i^{dataset} issue_i * magnitude * type * disease * size * vesselsize * location * lumenuncertainty)$$

In an exemplary embodiment, limits may be defined for the following criteria, and unacceptable scores may result in rejections of data for coronary blood flow modeling and simulations:
  image resolution: pixel size <0.5 mm
  slice thickness ≤1.0 mm
  number of scanner slices ≥64
  missing slices or missing data not acceptable
  must have sublingual nitrates at the time of CT acquisition
  coronary arteries and myocardium must be completely included in the dataset
  presence of anatomic abnormalities, such as severe congenital heart disease, are not acceptable
  presence of implanted devices, such as pacemakers, or prior surgeries, such as bypass grafts, are not acceptable In an exemplary embodiment, the following criteria may be defined at a local level. For example, for each image quality issue, a score of magnitude of the effect may be generated. Other information may be added, such as the location and size of the issue, based on the following:
  contrast level
  noise level
  misregistration or misalignment
  motion or blurring
  partial volume effect or blooming
  general uninterpretable or poorly defined regions Method 120 may further include calculating and outputting a total score of the regions of uninterpretability for the image as a quantitative metric of image quality (step 130). For example, in one embodiment, the scores for each issue weighted by size and location may be summed over each vessel and case.

Figure 5:
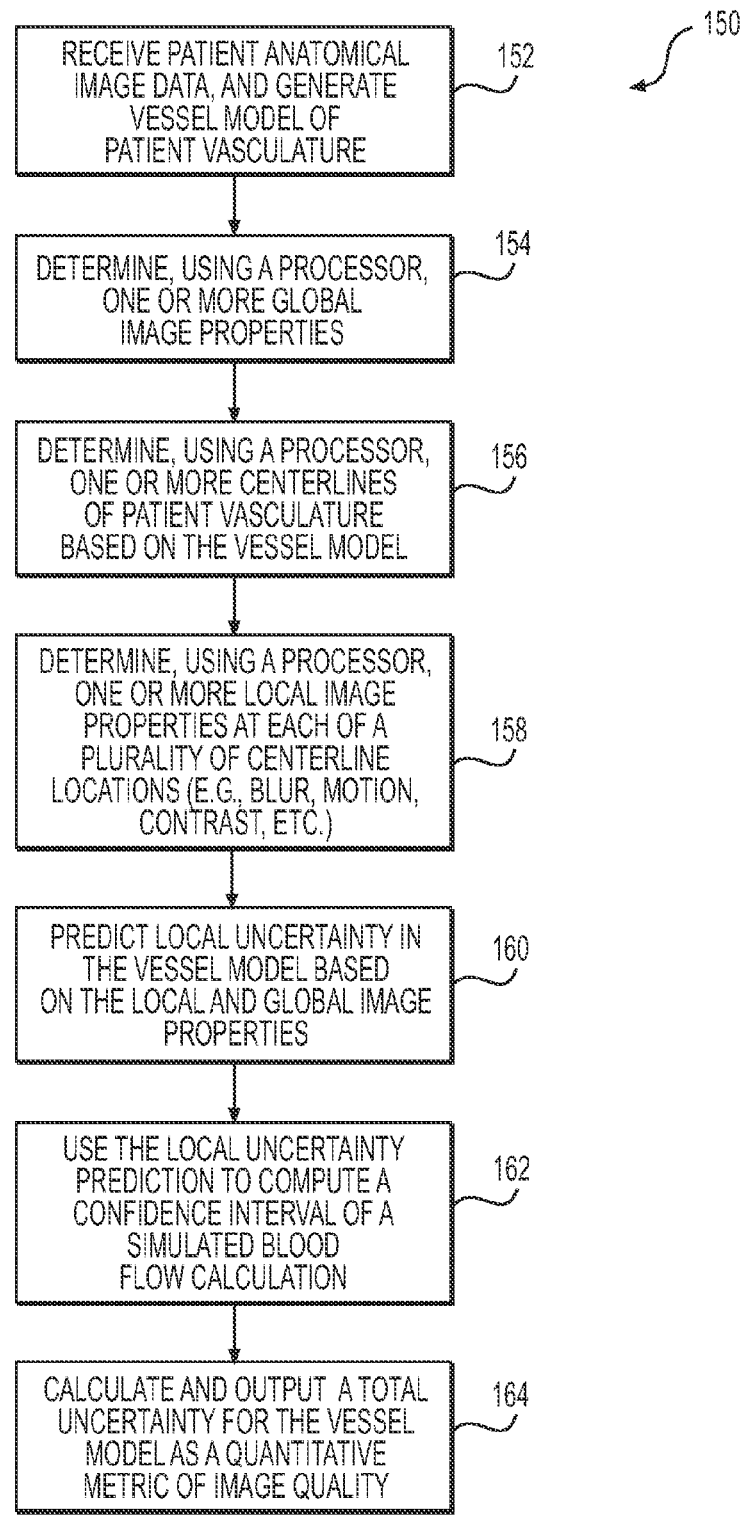
FIG. 5 is a flow chart that describes an exemplary process for performing computer-automated assessment of medical image quality, generation of image quality metrics, and use of image quality metrics, according to various exemplary embodiments.

FIG. 5 is a flow chart that describes an exemplary method 150 for performing computer-automated assessment of medical image quality, generation of image quality metrics, and use of image quality metrics, according to various exemplary embodiments. In one embodiment, method 150 may include receiving patient anatomical image data, and generating a vessel model of patient vasculature (step 152). Method 150 may further include determining, using a processor, one or more global image properties (step 154).

In an exemplary embodiment, the disclosed systems and methods may involve automatically assessing quantitative information that can be extracted from the imaging data including, but not limited to, the image resolution, slice thickness, reconstruction kernel, number of scanner slices, missing slices or missing data, and phase of acquisition. The information may be extracted by analyzing dimensions or tags in the image data (e.g., DICOM header). Each of these categories may have simple accept/reject criteria. The following serve as example specifications:
  image resolution: pixel size <0.5 mm
  slice thickness ≥0.9 mm
  reconstruction kernel equal to manufacturer specific filters
  number of scanner slices ≥64
  missing slices or missing data not acceptable
  phase of acquisition >65% and ≤80%

In an exemplary embodiment, the resolution, slice, phase, and data completeness may not have absolute accept/reject criteria, but rather a range of scores that will contribute to an overall image quality metric for the dataset. For example, resolution and slice thickness may be combined to obtain a voxel volume (e.g., 0.4 mm×0.4 mm×0.75 mm). Higher or lower resolutions may add or subtract from an overall dataset score.

In an exemplary embodiment, information regarding medication administered and heart rate during an imaging study may be submitted with the study to the computer system. The computer system may accept/reject a dataset based on this information, e.g., absence of sublingual nitrates may necessitate rejection of the dataset. Alternatively, the presence, absence, or dose of medication, the HR, or other physiologic metrics may contribute to the overall score or direct the method and computer system to perform modeling and simulation with different methods. For example, the absence of sublingual nitrates may direct the use of alternate coronary lumen segmentation algorithms to ensure proper vessel sizes.

In an exemplary embodiment, missing anatomic data, presence of anatomic abnormalities, and presence of implanted devices or prior surgeries may be detected by a user of the computer system. The presence or absence of these issues may add to a score or result in accept/reject decisions for the dataset. These assessments may also be automated.

Method 150 may further include determining, using a processor, one or more centerlines of patient vasculature based on the vessel model (step 156). Method 150 may further include determining one or more local image properties at each of a plurality of centerline locations (e.g., blur, motion, contrast, etc.) (step 158). In an exemplary embodiment, the computer system may be configured to automatically determine such local image properties, or local or global image quality, by implementing a fully automated quantitative assessment of the image quality, based on any one or more of the image quality issues described herein. For example, a processor of computer system 40 may automatically determine one or more local image properties in any of the manners discussed above with respect to the user-guided method of FIG. 4, except that computer system 40 may do so automatically, such as by executing an algorithm, in some cases according to the exemplary concepts described below.

In an exemplary embodiment, the contrast and noise levels may be assessed locally (e.g., at a section of a vessel) or globally (e.g., across multiple vessels or a large representative vessel or structure). This assessment may be performed by taking measurements of the contrast level (e.g., mean contrast in a region of interest) and noise level (e.g., standard deviation of contrast in a region of interest). These measurements may also be combined to create a signal to noise ratio by dividing the contrast and noise measurements. Additionally, the contrast and noise measurements may take into account background or surrounding tissue contrast and noise to represent the difference between the region of interest (e.g., coronary artery) and background data (e.g., myocardium and epicardial fat). Alternatively, the contrast, noise, and contrast to noise ratio may be assessed qualitatively on a local or global scale by rating the degree of noise in comparison to reference standards (e.g., 1=poor, 2=marginal, 3=good). In one embodiment, a processor of computer system 40 may calculate noise based on an algorithm that receives as inputs some CT volume data and aorta mask data (e.g., from zhf file), and that outputs an aorta mean Hounsfield Unit ("HU") value, noise standard deviation, surrounding mean HU value, and CNR. In one embodiment, a processor of computer system 40 may calculate contrast differences between left and right ventricles based on an algorithm that receives as inputs some CT volume and myomass (long axis and segmentation), and that outputs LV mean HU value and RV mean HU value.

In an exemplary embodiment, misregistration or misalignments may be detected by searching through the data or globally through the dataset or locally near the arteries to identify where offsets occur between adjacent images. These may be detected by a user or by the computer system. The degree of misregistration may be classified by the distance the data is shifted, the amount of a region that is affected (e.g., length of vessel that is affected), or by the orientation of the region affected (e.g., perpendicular or parallel to vessel). Alternatively, the misregistration may be assessed qualitatively on a local or global scale by rating the degree of misregistration in comparison to reference standards (e.g., 1=poor, 2=marginal, 3=good). In one embodiment, a processor of computer system 40 may calculate index-slice misregistration based on an algorithm that receives a CT image, outputs peaks locations, and scores values.

In an exemplary embodiment, motion or blurring artifact may be detected by scanning through the global data or locally near the arteries to identify areas where the image data is blurred or has soft edges (e.g., the edge of a vessel has soft and smeared edges). These may be detected by a user or by the computer system. The degree of motion may be classified by the distance the data blurred, the gradient of the image data, or other quantitative means. Alternatively, the motion may be assessed qualitatively on a local or global scale by rating the degree of motion in comparison to reference standards (e.g., 1=poor, 2=marginal, 3=good).

In an exemplary embodiment, partial volume or blooming artifacts may be detected by scanning through the global data or locally near the arteries to identify areas where the image data contains bright features that interfere with other parts of the data. These may be detected by a user or by the computer system. The degree of blooming may be classified by the intensity, the size, and/or a measurement of how far it spreads into neighboring structures (e.g., how much does blooming cover the lumen). Alternatively, the blooming may be assessed qualitatively on a local or global scale by rating the degree of blooming in comparison to reference standards (e.g., 1=poor, 2=marginal, 3=good).

In an exemplary embodiment, beam hardening may be detected by scanning through the data globally or locally near the arteries to identify areas where the image data contains dark spots or streaks that interfere with other parts of the data. These may be detected by a user or by the computer system. The degree of beam hardening may be classified by the intensity, the shape, and/or a measurement of how much it interferes with neighboring structures (e.g., how much does beam hardening obscure the lumen). Alternatively, the beam hardening may be assessed qualitatively on a local or global scale by rating the degree of beam hardening in comparison to reference standards (e.g., 1=poor, 2=marginal, 3=good).

In an exemplary embodiment, any other general characteristic affecting image quality may be detected by scanning through the global data or locally near the arteries to identify areas where the image data is not interpretable or where feature definition such as the lumen is poor. These may be detected by a user or by the computer system. These may be quantified by the degree to which they affect lumen quality compared to adjacent regions and by the amount affected. Alternatively, the characteristic may be assessed qualitatively on a local or global scale by rating the degree of characteristic in comparison to reference standards (e.g., 1=poor, 2=marginal, 3=good).

Method 150 may further include predicting local uncertainty in the vessel model based on the local and global image properties (step 160). For example, in certain embodiments, machine learning, regression, and other statistical techniques may be used to derive functions or models relating image quality to modeling, simulation, and performance. As described in the next section, these metrics may be adjusted to achieve different needs.

Method 150 may further include using the local uncertainty prediction to compute a confidence interval of a simulated blood flow calculation (step 162). Method 150 may further include calculating and outputting a total uncertainty for the vessel model as a quantitative metric of image quality (step 164).

Exemplary embodiments of the step (step 162) of using the local uncertainty prediction to compute a confidence interval of a simulated blood flow calculation will now be described in more detail. In an exemplary embodiment, metrics may be tuned and have various correlations or criteria associated with them to achieve purposes including but not limited to: assess sufficiency of data for automated modeling, assess sufficiency of data for user-guided interpretation and/or modeling, direct the method or system used to model data, accept/reject imaging data, determine which of a multitude of a received data is best for modeling (e.g., alternate phases or reconstructions), provide feedback on imaging data in order to obtain improved or corrected data, label results differently depending on the image quality scores, and provide confidence estimation depending on the uncertainty associated with the image quality issues. All of these purposes are within the context of measuring and predicting simulation and modeling accuracy, precision, and performance.

In an exemplary embodiment, criteria may be derived for relating the image quality metric to error of FFR simulation results versus a reference standard of measured FFR. Coronary vessels and/or full datasets that pass the criteria may be accepted for processing in order to ensure a certain level of accuracy and precision of the solution. Vessels or full datasets that fail the criteria may be correlated with having higher error than desired. Alternatively, vessels or full datasets that fail may be directed to other methods and or systems that can achieve higher accuracy.

In an exemplary embodiment, criteria may be derived relating the image quality metric to variability in simulated FFR results based on different users. Coronary vessels and/or full datasets that pass the criteria may be accepted for processing in order to ensure a certain level of precision of the solution. Vessels or full datasets that fail the criteria may be correlated with having higher variability than desired. Alternatively, vessels or full datasets that fail may be directed to other methods and or systems that can achieve higher precision.

In an exemplary embodiment, criteria may be derived relating the image quality metric to performance efficiency of modeling and simulating blood flow. Datasets above certain scores may be rejected, associated with a special processing fee, or may be directed to different resources to obtain a desired efficiency. Alternatively, an estimate of simulation cost and/or time may be provided based on the image quality score. For example, if the image quality is getting worse and worse, it may be possible to estimate higher cost or price associated with manually identifying and correcting image quality characteristics or anatomic characteristics.

In an exemplary embodiment, criteria may be derived to label results from FFR simulations that are performed in coronary vessels and/or full datasets that contain a region of low image quality that fails to meet the criteria. Such labels may serve to provide indication that there is uncertainty in the solution in that region of the model and/or to explain what is modeled in light of the uncertainty (e.g., an assumption).

In an exemplary embodiment, criteria may be derived to label regions in models that require special processing to ensure accuracy (e.g., inspection, different algorithm, expert review).

In an exemplary embodiment, criteria may be set to use certain methods in determining vessel size in the presence of certain image quality issues. For example, when a blooming artifact around calcified plaque is present, methods and systems for determining the lumen boundary (and subsequently blood flow) near the artifact may differ from those in the absence of artifact.

In an exemplary embodiment, criteria may be derived to assess the uncertainty or confidence of FFR simulation results that are performed in coronary vessels and/or full datasets that contained a region of low image quality that failed to meet the criteria. The uncertainty or confidence may result in the FFR results being reported with a % confidence or a confidence interval based on the effect of image quality (e.g., FFR is 0.87+/−0.05 or FFR is <0.80 with 76% confidence).

In an exemplary embodiment, criteria may be derived relating the image quality metric to error of FFR simulation results versus a reference standard of measured FFR. Coronary vessels and/or full datasets may be ranked on their scores against this criteria to determine which of a multitude of data would be best for simulating FFR results and obtaining the highest accuracy.

In an exemplary embodiment, at least one computer system may be located or rapidly accessible from the site where imaging data is created. Criteria may be set to assess the image quality as it relates to impacting or predicting FFR simulation results. Coronary vessels and/or full datasets may be ranked on their scores against this criteria to provide instant feedback such that the site creating the imaging data could correct or update data until it meets the criteria needed to obtain desirable accuracy. Alternatively, instant feedback could be provided with an estimate or confidence associated with a reduced accuracy, allowing the site creating the imaging data to accept a lower accuracy if there is clinical benefit.

Figure 6:
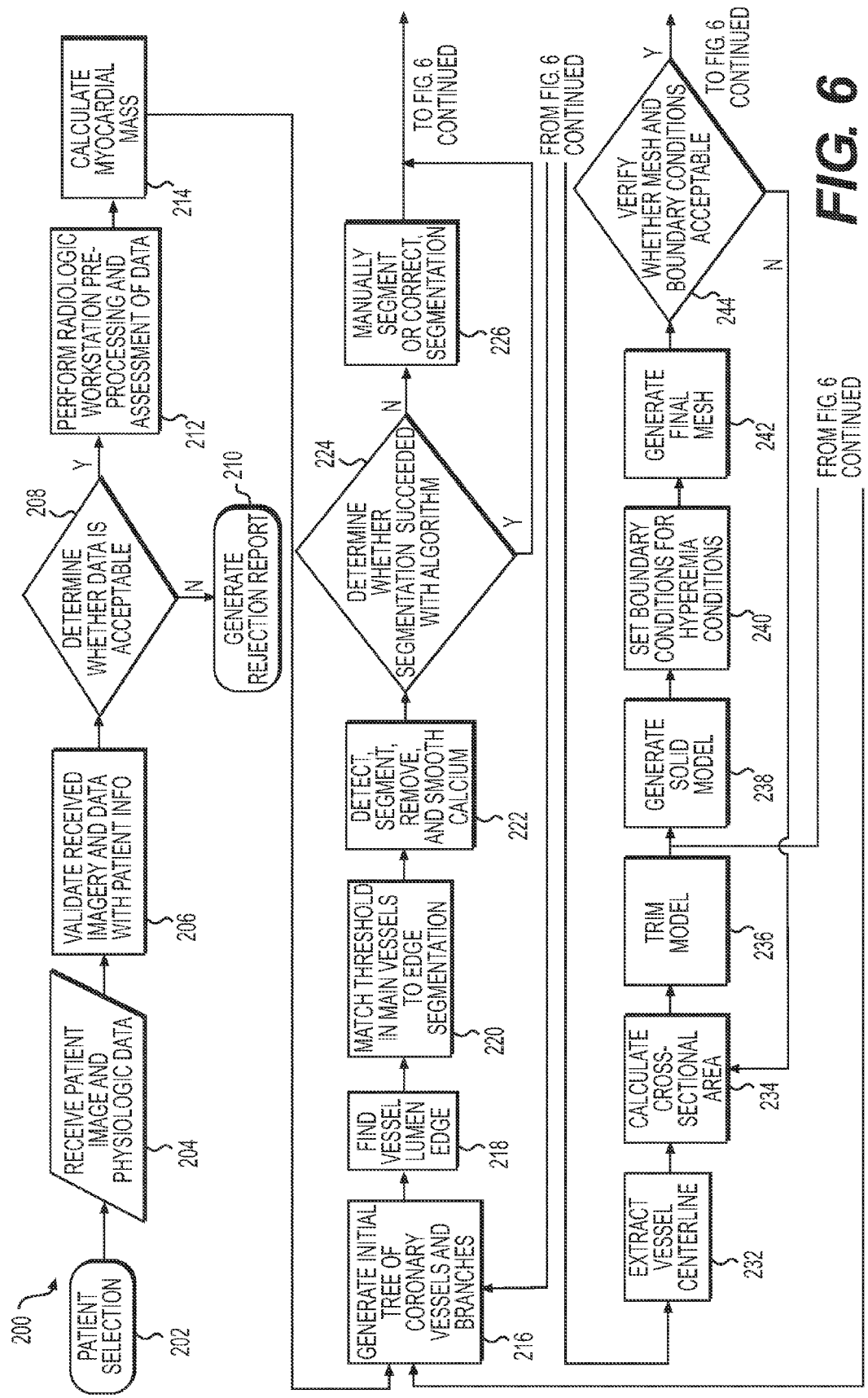
FIG. 6 is a flow chart that describes an exemplary process for assessing medical image quality, generating image quality metrics, and using image quality metrics, in the context of estimating coronary fractional flow reserve values, according to various exemplary embodiments.
Figure 6:
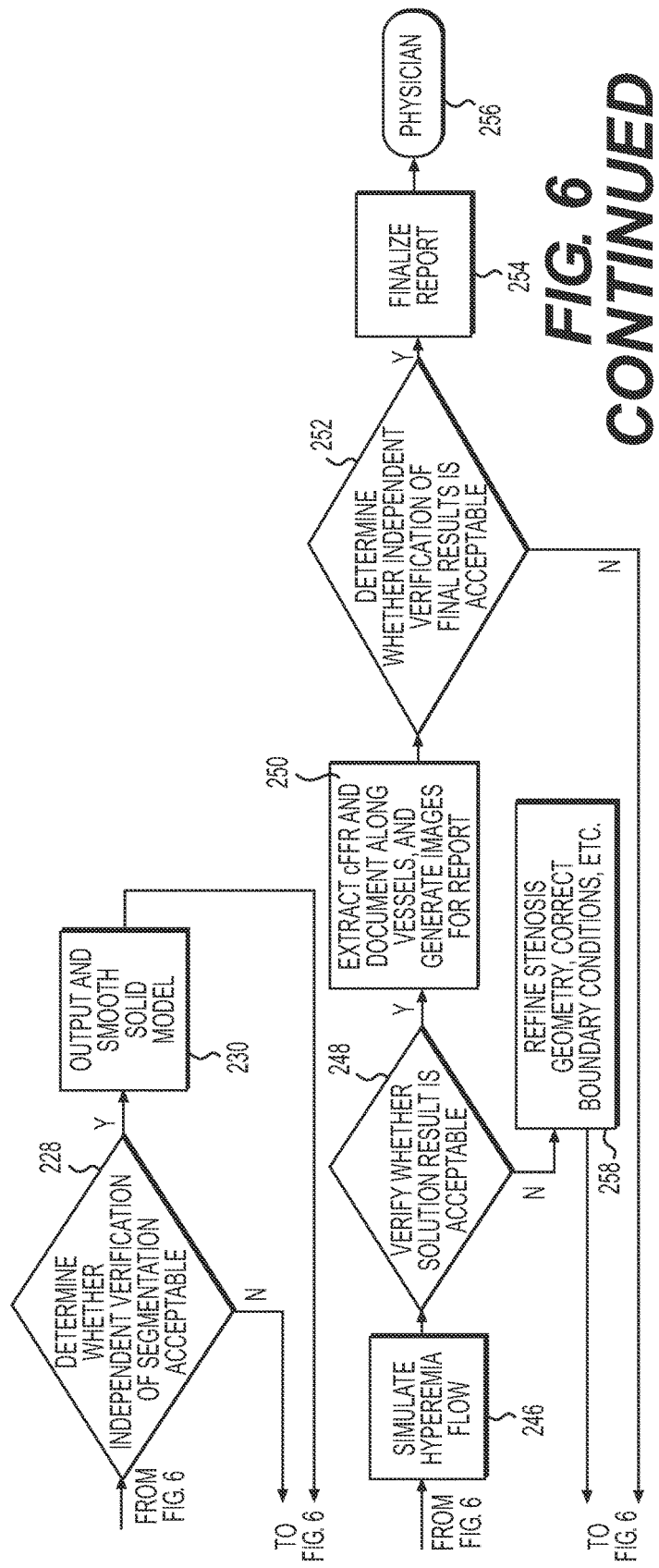

FIG. 6 is a flow chart that describes an exemplary method 200 for assessing medical image quality, generating image quality metrics, and using image quality metrics, in the context of estimating coronary fractional flow reserve values, according to various exemplary embodiments. For example, FIG. 6 depicts a method of estimating coronary fractional flow reserve (FFR) values based on certain image quality assessment techniques disclosed herein, and FFR calculation techniques described in U.S. Pat. No. 8,315,812.

As shown in FIG. 6, method 200 may begin by selecting a particular patient (step 202) and receiving patient image and physiologic data (step 204). Method 200 may include validating the received imagery and data with known patient information (step 206), for example, for user identity or privacy reasons. Method 200 may include determining whether the received data is acceptable (step 208). For example, step 208 may include either accepting or rejecting each of one or more received images based on any one or combination of the image assessment and scoring techniques disclosed herein. If any one or more images are rejected, method 200 may include generating a rejection report (step 210). For example, the method may include obtaining images that are rejected and providing feedback to the user on the rejected images, to assist the user in obtaining new images that would not be rejecting. For example, the computer system may send to a technician, physician, or any other healthcare professional, a report of rejected images along with guidelines and/or recommendations for adjusting image acquisition parameters that would enable obtaining images of higher image quality scores. Such reports, rejected images, guidelines, and/or recommendations may be displayed to a physician, technician, or any other healthcare provider, whether through an electronic display and/or over an electronic network.

If the data is acceptable, then method 200 may include performing radiologic workstation pre-processing and assessment of data (step 212). Method 200 may then include calculating myocardial mass (step 214), generating an initial tree of coronary vessels and branches (step 216), finding one or more vessel lumen edges (step 218), matching thresholds in main vessels to edge segmentations (step 220), and detecting, segmenting, removing, and smoothing any plaque or calcium (step 222). Method 200 may then include determining whether segmentation succeeded using an algorithm (step 224). If not, then method 200 may include manually segmenting or correcting the segmentation (step 226). If segmentation succeeded, then method 200 may include determining whether independent verification of segmentation is acceptable (step 228). If not, then method 200 may return to step 216 of generating the initial tree of coronary vessels and branches.

If segmentation was acceptable (step 228; Yes), then method 200 may include outputting and smoothing a solid model (step 230), extracting one or more vessel centerlines (step 232), calculating vessel cross-sectional areas (step 234), trimming the model (step 236), generating a solid model (step 238), setting boundary conditions for hyperemia conditions (step 240), and generating a final mesh (step 242). Method 200 may then include verifying whether mesh and boundary conditions are acceptable (step 244). If not, then method 200 may return to step 234 of calculating cross-sectional area.

If mesh and boundary conditions are acceptable (step 244; Yes), then method 200 may include simulating hyperemia flow (step 246) and verifying whether the solution result is acceptable (step 248). If not, then method 200 may include refining stenosis geometry, correcting boundary conditions, etc. (step 258). If the solution result is acceptable (step 248; Yes), then method 200 may include extracting cFFR, documenting the same along the vessels, and generating images for a report (step 250). Method 200 may then include determining whether independent verification of the final results is acceptable (step 252). If not, then method 200 may include returning to step 216 of generating the initial tree of coronary vessels and branches.

If the independent verification of the final results is acceptable (step 252; Yes), then method 200 may include finalizing a report (step 254) and forwarding the finalized report to the physician (step 256).

Figure 7A:
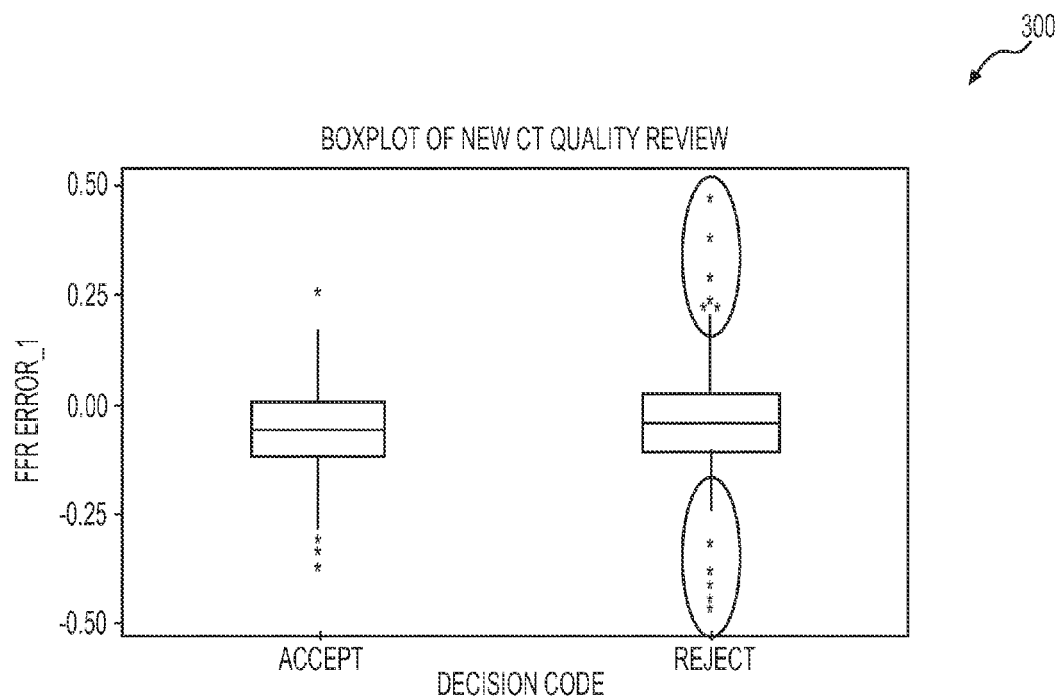
FIG. 7A is an exemplary box plot of fractional flow reserve error and acceptance or rejection based on CT image quality review, according to various exemplary embodiments.

FIG. 7A is an exemplary box plot of fractional flow reserve error and acceptance or rejection based on CT image quality review, according to various exemplary embodiments. For example, the box plot of FIG. 7A may illustrate that rejected cases may have more variation of FFRct error than do the accepted cases.

Figure 7B:
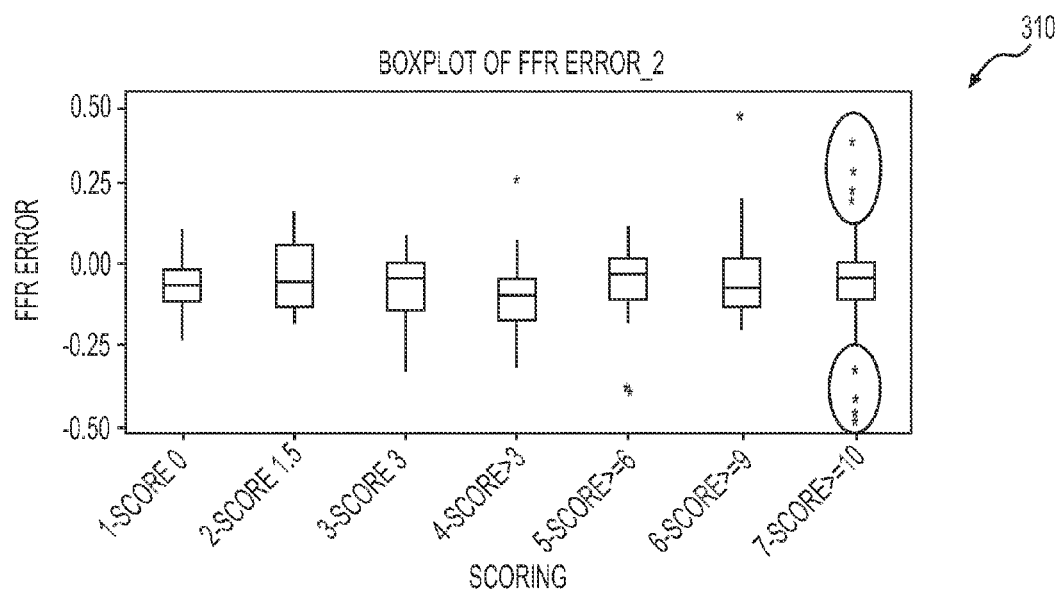
FIG. 7B is an exemplary box plot of fractional flow reserve error and scoring based on CT image quality review, according to various exemplary embodiments.

FIG. 7B is an exemplary box plot of fractional flow reserve error and scoring based on CT image quality review, according to various exemplary embodiments. For example, the box plot of FIG. 7B may illustrate that variation of FFRct error may increase as an image quality penalty score increases. In other words, cases having a score between 7 and 10 may have substantially higher variation in FFRct error than cases having a score between 0 and 1.

FIG. 8 is an exemplary bar graph depicting comparisons between quality of fractional flow reserve and computed tomography based on image quality by number of vessels, according to various exemplary embodiments. Specifically, the bar graph of FIG. 8 may depict performance as correlated to vessel-specific quality ratings of CT interpretability.

Figure 10:
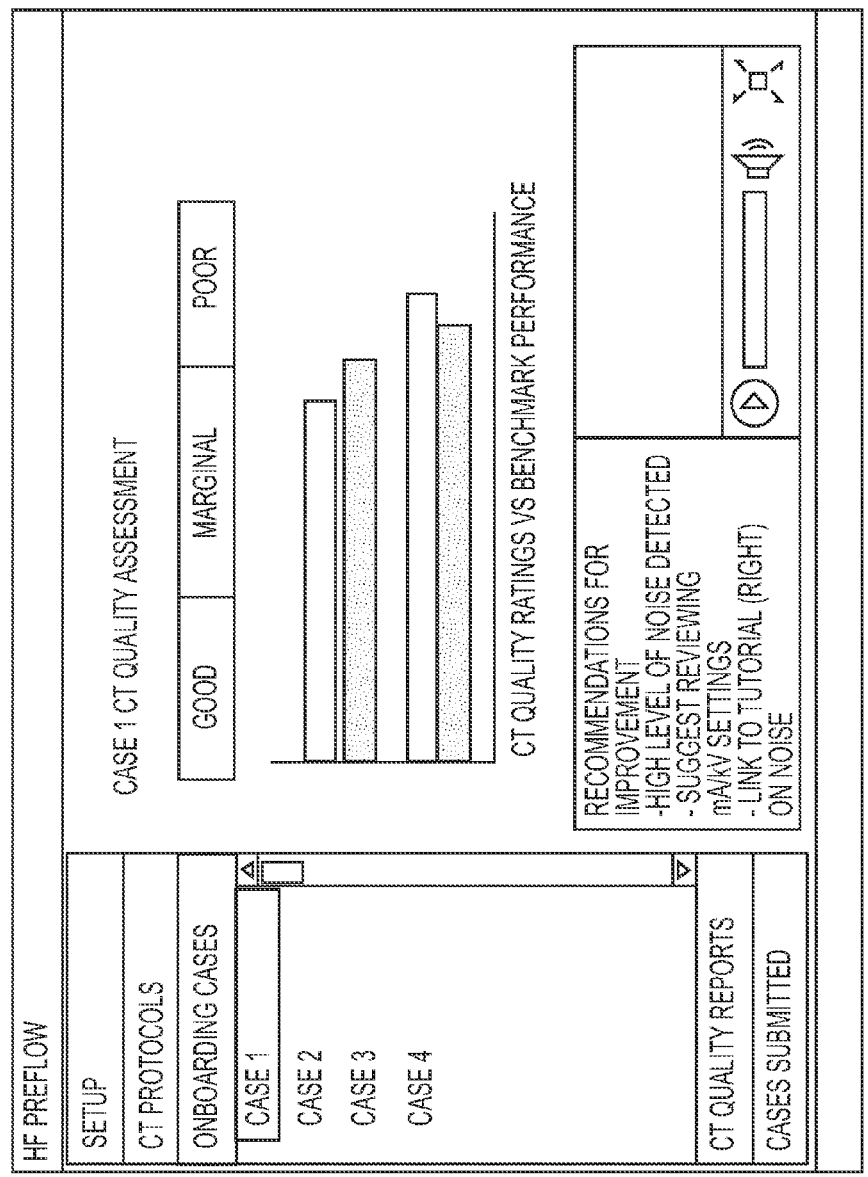
FIG. 10 is a screenshot of an exemplary interface for displaying computed tomography quality ratings vs. benchmark performance, according to various exemplary embodiments.

FIG. 10 is an exemplary screenshot depicting computed tomography quality ratings vs. benchmark performance, according to various exemplary embodiments. For example, as shown in FIG. 10, a processor of computer system 40 may provide a user interface by which a user, such as an image technician, physician, or any other health care provider, may review a CT image quality assessment for each of a plurality of patients or "cases." As shown in FIG. 10, in one embodiment, each case may be displayed as having one of "Good," "Marginal," or "Poor" image quality. The image quality may also be compared, such as by display in a bar or other chart, with certain benchmark performance standards of image quality. The interface may generate and display quality reports, and/or make recommendations for improving the obtained quality. By way of example, if a high level of noise is detected, the user interface may suggest reviewing the "mA/kV settings," and may provide a link to a tutorial on noise. Of course, the user interface and guidelines may provide the user with an assessment of image quality and recommendations for improving image quality in relation to any of the image quality issues discussed herein.

The presently disclosed systems and methods may enable the automatic estimation and correction of image quality issues, thereby reducing human time and variability before now associated with quality control review of image data. Moreover, the presently disclosed systems and methods may provide better understanding of a relationship between simulation and modeling accuracy (e.g., FFR error) and image quality scores. Still further, the presently disclosed systems and methods may enable users to better and automatically select a desirable base phase of image for analyst review, and provide better "red flags" for further review or rejection of certain scans.

In one embodiment, the presently disclosed techniques may include defining input uncertainties, calculating FFR analysis sensitivities, and calculating confidence intervals in FFR, according to any of the techniques described in U.S. application Ser. No. 13/864,996, filed Apr. 17, 2013, the entirety of which is incorporated herein by reference.

In one embodiment, the presently disclosed techniques may include performing any of the various presolving techniques described in U.S. application Ser. No. 13/625,628, filed Sep. 24, 2012, the entirety of which is incorporated herein by reference.

In one embodiment, FFR values may be obtained using machine learning estimates as opposed to physics-based simulations. In other words, instead of executing a coronary solver, such as in the '812 patent, for each of the plurality of collocation points, the disclosed systems and methods may efficiently estimate blood flow characteristics based on knowledge gleaned from analyzing blood flow of numerous other patients. For example, the disclosed systems and methods may include performing any of the various machine learning techniques described in U.S. Provisional Patent Application No. 61/700,213, filed Sep. 12, 2012, the entirety of which is incorporated herein by reference. Thus, in one embodiment, FFR values may be obtained by training a machine learning algorithm to estimate FFR values for various points of patient geometry based on feature vectors of patient physiological parameters and measured blood flow characteristics, and then applying the machine learning algorithm to a specific patient's geometry and physiological parameters to obtain predicted FFR values.

One or more of the steps described herein may be performed by one or more human operators (e.g., a cardiologist or other physician, the patient, an employee of the service provider providing the web-based service or other service provided by a third party, other user, etc.), or one or more computer systems used by such human operator(s), such as a desktop or portable computer, a workstation, a server, a personal digital assistant, etc. The computer system(s) may be connected via a network or other method of communicating data.

Any aspect set forth in any embodiment may be used with any other embodiment set forth herein. Every device and apparatus set forth herein may be used in any suitable medical procedure, may be advanced through any suitable body lumen and body cavity, and may be used for imaging any suitable body portion.

Various modifications and variations can be made in the disclosed systems and processes without departing from the scope of the disclosure. Other embodiments will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method for automatically selecting image(s) to produce model(s) for a patient-specific simulation of blood flow, using at least one computer system, the method comprising:
   receiving one or more images of at least a portion of a patient's anatomy;
   obtaining one or more image properties of the received images using one or more processors of the at least one computer system;
   obtaining, for a selected one of the received images, an identification of one or more image characteristics of the selected one of the received images, where the one or more image characteristics are associated with an anatomic feature of the patient's anatomy;
   identifying a type of patient-specific simulation to perform using the received images;
   receiving, for the type of patient-specific medical simulation using the received images, a selected level of simulation accuracy, precision, or performance;
   quantifying a minimum image quality to render the received selected level of simulation accuracy, precision, or performance;
   generating an image assessment based on the quantified minimum image quality, and the one or more image properties or image characteristics; and
   applying the image assessment to each of the received images to select one or more images to produce one or more models for a patient-specific simulation of blood flow.

2. The method of claim 1, further comprising:
   combining or correcting one or more of the selected images to generate a model for a patient-specific simulation of blood flow.

3. The method of claim 1, further comprising:
   guiding simulation techniques based on the selected level of accuracy, precision, or performance.

4. The method of claim 1, further comprising:
   performing, using a processor of the computer system, a patient-specific simulation of blood flow using one or more of the selected images.

5. The method of claim 4, further comprising:
   performing anatomic localization of the at least a portion of the patient's anatomy based on the received images, wherein the simulation is based on the anatomic localization of the at least a portion of the patient's anatomy.

6. The method of claim 1, further comprising:
   estimating performance metrics based on time to complete a simulation or cost of a simulation, wherein the image assessment is based on the estimated performance metrics.

7. The method of claim 1, further comprising:
   calculating an image quality score based on the one or more image properties or the one or more image characteristics, wherein the image assessment is based on the image quality score.

8. The method of claim 1, wherein the one or more image characteristics include one or more of: a local contrast level, a local noise level, a misregistration, a misalignment, a local motion anomaly, a local blurring anomaly, a partial volume effect, a blooming effect, and an artifact.

9. The method of claim 1, wherein the one or more image properties include one or more of: an image resolution, a medical anatomy slice thickness, a number of scanner slices, a medication parameter, and a patient characteristic.

10. The method of claim 1, further comprising:
    generating and transmitting a rendering of a recommendation to perform or not perform patient-specific medical simulation based on the image assessment.

11. A system for automatically selecting image(s) to produce model(s) for a patient-specific simulation of blood flow, the system comprising:
    a digital storage device storing instructions for assessing the quality of medical images of at least a portion of a patient's anatomy; and
    a processor configured to execute the instructions to perform a method including:
      receiving one or more images of at least a portion of a patient's anatomy;
      obtaining one or more image properties of the received images using one or more processors of the at least one computer system;
      obtaining, for a selected one of the received images, an identification of one or more image characteristics of the selected one of the received images, where the one or more image characteristics are associated with an anatomic feature of the patient's anatomy;
      identifying a type of patient-specific simulation to perform using the received images;
      receiving, for the type of patient-specific simulation using the received images, a selected level of accuracy, precision, or performance;
      quantifying a minimum image quality to render the received selected level of accuracy, precision, or performance;
      generating an image assessment based on the quantified minimum image quality, and the one or more image properties or image characteristics; and
      applying the image assessment to each of the received images to select one or more images to produce one or more models for a patient-specific simulation of blood flow.

12. The system of claim 11, wherein the processor is further configured for:
    combining or correcting one or more of the selected images to generate a model for a patient-specific simulation of blood flow.

13. The system of claim 12, wherein the processor is further configured for:
    guiding simulation techniques based on the selected level of accuracy, precision, or performance.

14. The system of claim 11, wherein the processor is further configured for:
    performing, using a processor of the computer system, a patient-specific simulation of blood flow using one or more of the selected images.

15. The system of claim 14, wherein the processor is further configured for:
    performing anatomic localization of the at least a portion of the patient's anatomy based on the received images, wherein the simulation is based on the anatomic localization of the at least a portion of the patient's anatomy.

16. The system of claim 11, wherein the processor is further configured for:
    estimating performance metrics based on time to complete a simulation or cost of a simulation, wherein the image assessment is based on the estimated performance metrics.

17. The system of claim 11, wherein the processor is further configured for:
    calculating an image quality score based on the one or more image properties or the one or more image characteristics, wherein the image assessment is based on the image quality score.

18. The system of claim 11, wherein the one or more image characteristics include one or more of: a local contrast level, a local noise level, a misregistration, a misalignment, a local motion anomaly, a local blurring anomaly, a partial volume effect, a blooming effect, and an artifact.

19. The system of claim 11, wherein the one or more image properties include one or more of: an image resolution, a medical anatomy slice thickness, a number of scanner slices, a medication parameter, and a patient characteristic.

20. A non-transitory computer readable medium for use on at least one computer system containing computer-executable programming instructions for automatically selecting image(s) to produce model(s) for a patient-specific simulation of blood flow, that when executed by the at least one computer system, cause the performance of a method comprising:

receiving one or more images of at least a portion of a patient's anatomy;

obtaining one or more image properties of the received images using one or more processors of the at least one computer system;

obtaining, for a selected one of the received images, an identification of one or more image characteristics of the selected one of the received images, where the one or more image characteristics are associated with an anatomic feature of the patient's anatomy;

identifying a type of patient-specific medical modeling or simulation to perform using the received images;

receiving, for the type of patient-specific medical modeling or simulation using the received images, a selected level of accuracy, precision, or performance;

quantifying a minimum image quality to render the received selected level of accuracy, precision, or performance;

generating an image assessment based on the quantified minimum image quality, and the one or more image properties or the image characteristics; and applying the image assessment to each of the received images to select one or more images to produce one or more models for a patient-specific simulation of blood flow.

* * * * *